(12) United States Patent
Axelgaard et al.

(10) Patent No.: US 6,850,791 B1
(45) Date of Patent: Feb. 1, 2005

(54) COMPRESS GARMENT WITH COVER FOR ELECTRODES

(75) Inventors: Jens Axelgaard, Fallbrook, CA (US); George Cornell, Vista, CA (US); Steve Heard, Escondido, CA (US)

(73) Assignee: Axelgaard Manufacturing Co. Ltd., Fallbrook, CA (US)

( * ) Notice: Subject to any disclaimer, the term of this patent is extended or adjusted under 35 U.S.C. 154(b) by 0 days.

(21) Appl. No.: 10/384,142

(22) Filed: Mar. 7, 2003

Related U.S. Application Data

(62) Division of application No. 09/748,548, filed on Dec. 26, 2000, now Pat. No. 6,571,115.

(51) Int. Cl.[7] .................................................. A61B 5/04
(52) U.S. Cl. ...................................... 600/388; 607/149
(58) Field of Search .......................... 128/897; 600/372, 600/382, 386, 388–390, 393; 601/15; 602/1, 60–62; 607/115, 149, 152

(56) References Cited

U.S. PATENT DOCUMENTS

| | | | | |
|---|---|---|---|---|
| 2,943,627 A | * | 7/1960 | Howell | 607/152 |
| 4,125,110 A | * | 11/1978 | Hymes | 600/391 |
| 4,583,547 A | * | 4/1986 | Granek et al. | 600/388 |
| 5,007,427 A | * | 4/1991 | Suzuki et al. | 600/436 |
| 5,643,329 A | * | 7/1997 | Solomonow et al. | 607/43 |
| 5,865,740 A | * | 2/1999 | Kelly et al. | 600/382 |
| 5,995,861 A | * | 11/1999 | Price | 600/372 |
| 6,259,939 B1 | * | 7/2001 | Rogel | 600/390 |
| 6,571,115 B2 | * | 5/2003 | Axelgaard et al. | 600/388 |

FOREIGN PATENT DOCUMENTS

| | | | |
|---|---|---|---|
| DE | 4210684 | * | 10/1993 |
| JP | 406070897 | * | 3/1994 |

* cited by examiner

Primary Examiner—Kennedy Schaetzle
Assistant Examiner—Kristen Mullen
(74) Attorney, Agent, or Firm—Walter A. Hackler

(57) ABSTRACT

A compress garment for application to a body generally includes a member sized and shaped for positioning onto a body when in position conforms to and supports a body shape. A least one, preferably a multiple number of access windows disposed in the garment member for enabling dermal application and removal of a medical electrode. The access windows are located on the garment member at positions enabling access to pre-selected dermal areas.

3 Claims, 4 Drawing Sheets

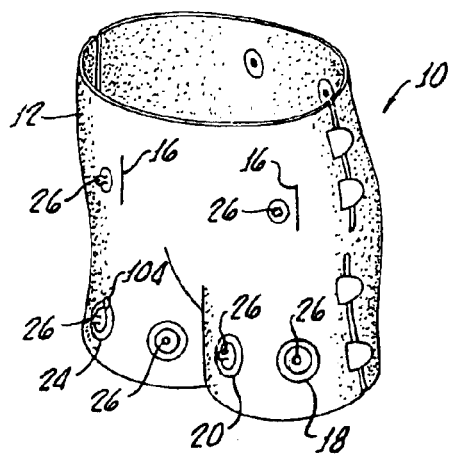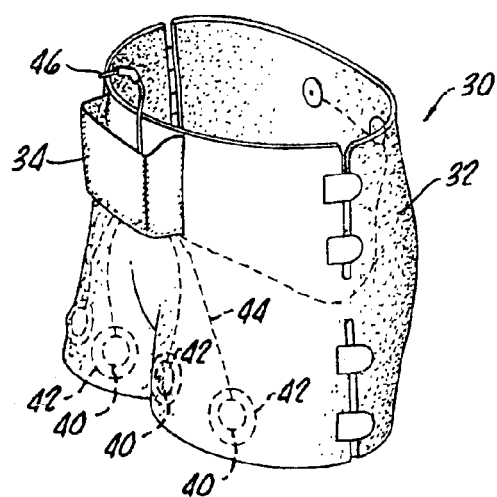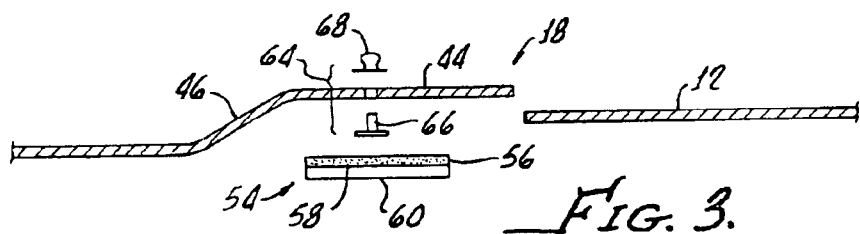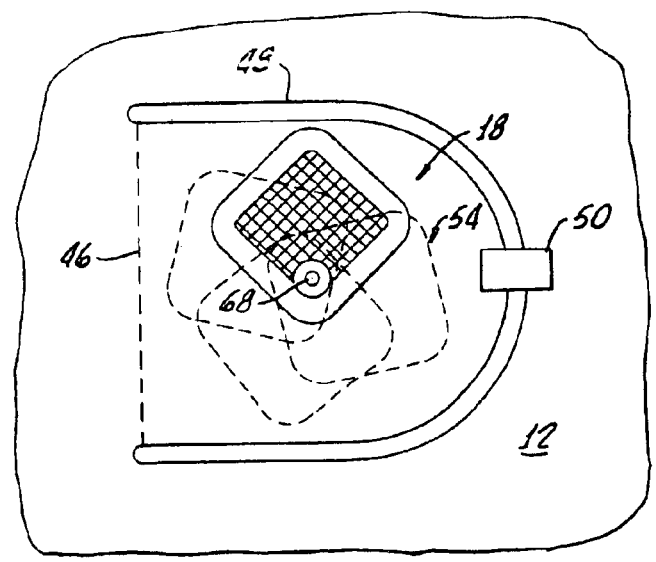

COMPRESS GARMENT WITH COVER FOR ELECTRODES

The present application is a division of U.S. Ser. No. 09/748,548 filed on Dec. 26, 2000 now U.S. Pat. No. 6,571,115.

The present invention generally relates to a compress garment, and more specifically is directed to a compress garment for positioning medical electrodes against a body.

Monitoring electrodes are well known for their use in determining a multitude of body conditions.

Transcutaneous electrical nerve stimulation is used for example, in post-operative and chronic pain control.

On the other hand, muscle stimulation is useful for example, in maintenance and development of muscle tissue and is a particularly important function in sports medicine.

While significant advantages afforded through the use of electrical stimulation of nerves and muscles, its effectiveness can be enhanced when used in combination with a supporting compress, band or brace, which may not only provide for immobilization of the body part, but also proper placement and positioning of electrical stimulation electrodes with respect to the body part. Reference is made to U.S. patent application entitled "ELECTRICAL STIMULATION COMPRESS" Ser. No. 09/428,196 filed Oct. 27, 1999. This patent application is to be incorporated herewith in its entirety, including all specifications and drawings by this specific reference thereto. The referenced patent application is limited to relatively small supports, bands, or braces because of the difficulty in placement of electrodes thereunder. For large compresses, or garments, such as for example, sleeves and torso garments, it is difficult to effect proper placement of the electrodes because the "skin tight" nature of the garment. Such garments must be rolled, pulled over, strapped or slid into position in order to effect proper compress or bracing for the patient. It is also evident that electrode placement, or the means therefore, should not interfere with the purpose of the garments.

The present invention provides for the use of difficult to don compress garments in combination with accurate placement of one or more medical electrodes without interfering with the garment placement or function.

SUMMARY OF THE INVENTION

A compress garment in accordance with the present invention for application to a body generally includes a garment member sized and shaped for positioning onto a body, and when in position, conforming to and supporting a body shape. The positioning may be by sliding, rolling or strapping the garment member onto the body. Typically the garment member is elastic and of sufficient elasticity to not only conform to the body part but act also as a brace or compress. Such garment members cover a large area of body and are custom made and fitted to a patient in order to apply compress, or support, to selected body parts as noted hereinabove.

In accordance with the present invention, at least one access window is disposed in the garment member for enabling dermal application and removal of a medical electrode. The access window is located on the garment member at a position enabling access to a pre-selected dermal area.

In one embodiment of the present invention, the access window comprises a slit in the garment member and the slit is sized and shaped for enabling the insertion and removal of a medical electrode therethrough. Further, an electrical contact for example, an eyelet of a snap assembly, is disposed in the garment member and passes through the garment member proximate the slit for establishing electrical connection with the medical electrode. In this embodiment, the medical electrode has no separate electrical lead wires extending therefrom.

In another embodiment of the present invention, the access window comprises at least one hinged flap with the hinged flap being sized and shaped for enabling insertion and removal of the medical electrode thereunder. In addition, an electrical contact, passing through the hinged flap is provided for establishing electrical connection with the medical electrode.

In yet another embodiment of the present invention, the access window may comprise an opening in the member with the opening being sized and shaped for enabling insertion and removal of a medical electrode. The garment further comprises a cover for covering the opening and the medical electrode. In addition, an electrical contact passing through the cover, may be provided for establishing electrical connection with the medical electrode.

A carrier, for example, a pocket, may be provided in the garment for supporting an electrical/electronic module for connection to the medical electrode. In this instance electrical connection between the electrode and the module may be through wires embedded in the garment.

BRIEF DESCRIPTION OF THE DRAWINGS

The advantages and features of the present invention will be better understood by the following description when considered in conjunction with the accompanying drawings in which:

FIG. 1 is a perspective view of a compress garment in accordance with the present invention showing a plurality of access windows and slits with electrical contact snaps extending therethrough;

FIG. 2 is a compress garment similar to that shown in FIG. 1 also featuring a pocket for supporting an electrical module and a plurality of electrodes disposed through access windows with wires integral with or beneath the garment for attachment to the electronic module (not shown) which may be disposed in the pocket;

FIG. 3 is a cross-section exploded view of an access window flap in accordance with the present invention;

FIG. 4 is a plan view of the flap access window as shown in FIG. 3 illustrating a variety of electrode positions;

DETAILED DESCRIPTION

Figure 5:
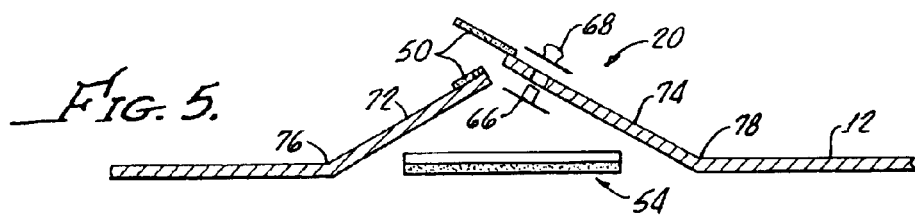
FIG. 5 is a cross-sectional view of an alternative flap access window in accordance with the present invention.

With reference to FIG. 1, there is shown a compress garment 10, specifically a lower torso garment, for application to a body. It should be appreciated that while a lower torso garment 10 is shown, other garment such as sleeves, leggings, upper torso garments or any garment covering large areas of the body are to be considered within the scope of the present invention.

Such garments are typically custom fitted to a patient and even light adhesion to the skin hampers donning and doffing of such garments. Prior art garments, not shown, utilizing stimulation electrodes, see for example the referenced patent application Ser. No. 09/428,196, further hamper the donning and doffing of the garments. The prior art has attempted to solve this problem though the use of sliding electrodes, however, the manufacture of such electrodes is difficult, and further, when sliding over the skin such slidable electrodes leave an undesirable "snail trail".

With further reference to FIG. 1, the garment 10 includes a sized member 12 which is shaped for slidable positioning onto a body, and when in position conforming to an supporting the body shape. In the present described embodiment 10, the shape is for the lower torso.

Various access windows 16, 18, 20, 22, 24 are shown disposed in the garment member 12 for enabling dermal application and removal of a medical electrode (not shown in FIG. 1) with the access window 16, 18, 20, 22, 24 being located on the garment member at positions enabling access to a preselected dermal area (disposed beneath the access windows). The positioning of the window 16, 18, 20, 22, 24 shown in the Figure is only intended to be a representation and not limiting the present invention to such limited positions. Fixed art positions are determined by a professional in the art of electrode placement. Also shown, are electrical snap connectors 26 described hereinafter in greater detail.

An alternative compress garment embodiment 30 is shown in FIG. 2 including a garment member 32 along with a pocket 34 for supporting an electrical module for connection to medical electrodes 40 shown in dashed line beneath access windows 42 and directly interconnected to the pocket through embedded wires 44 to a plug 46 for connecting with an electronic module (not shown). It should be appreciated that the electrodes 40 may be monitoring or stimulation electrodes, accordingly, a corresponding electronic module (not shown) is utilized.

With reference to FIG. 3, there is shown the flap window access 18 which includes a flap 44 with a hinge 46 integral with the garment member 12. The flap 18 may be cut from the garment member 12 and a circumferential band 48 disposed therearound, which may include an attachment system for providing a positive coupling between the flap 18 and the garment member 12. Any suitable attachment system, for example Velco® may be used in accordance with the present invention. In addition, a separate flap closure tab 50 may be included to provide tension and a smooth surface between the flap 18 and the garment member 12, see FIG. 4.

The flap 18 is sized and shaped for enabling insertion and removal of a medical electrode 54 which preferably includes a highly conductive gel 56, a conductive layer 58 and a skin specific gel 60. The electrode 54 is fully described in the referenced patent application Ser. No. 09/428,196 which is incorporated herewith, and accordingly, further specific details of the electrode 54 construction are omitted herewith for brevity.

The electrode 54 is electrically connected through the flap 44 by means of an electrical connector 64 passing through the hinged flap 44 and including a snap eyelet 66 and a snap stud 68.

As shown in FIG. 4 within the flap 18 area, the electrode 54 may be oriented in various positions as shown in a broken line.

With reference to FIG. 5, there is shown the access window 20 which includes, alternatively, two flaps 72, 74 having integral hinges 76, 78 symmetrical with the garment member 12. Common reference numerals shown in FIG. 5 being identical or substantially equivalent to the elements referenced to hereinbefore with the same reference characters.

Figure 6:
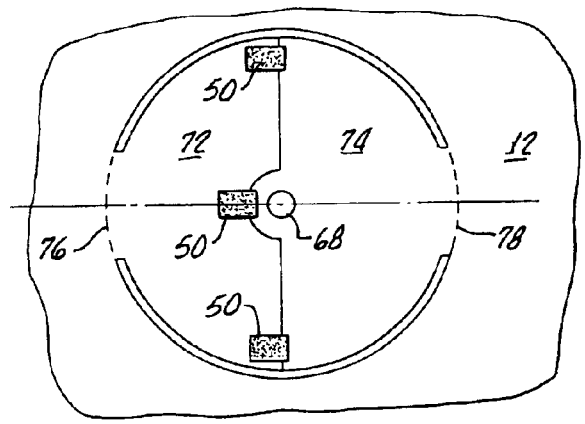
FIG. 6 is a plan view of the flap access window shown in FIG. 5.

FIG. 6 is a plan view of the window access 20 as shown in FIG. 5.

Figure 7:
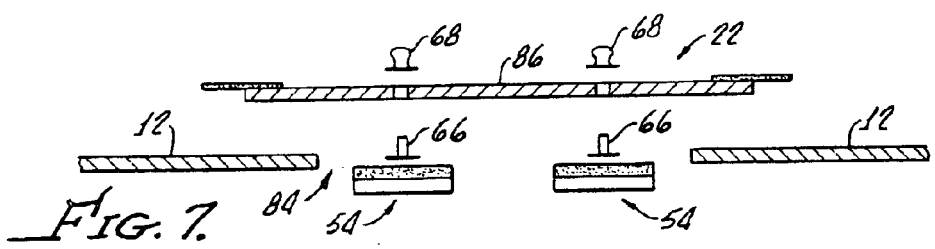
FIG. 7 is a cross-sectional exploded view of an access window and cover in accordance with the present invention sized for accommodating two electrodes, for example, an anode and cathode electrode, as may be desired in certain treatments or applications.
Figure 8:
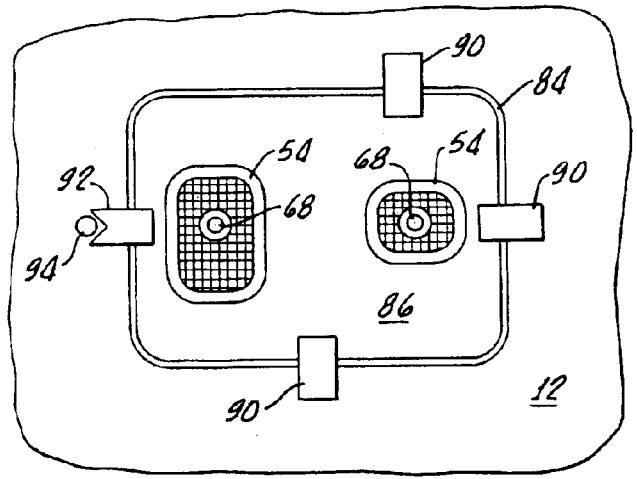
FIG. 8 is a plan view of the cover access window shown in FIG. 7 utilizing attachment tabs disposed in an asymmetric position around a window opening or alternately, an index for orienting the electrode beneath the cover.

With reference to FIGS. 7 and 8, there is shown the access window 22 which includes an opening 84 in the garment member 12 with the opening 84 being sized and shaped for the insertion or removal of a plurality of medical electrodes 54 and a cover 86 for covering the opening 84 and electrodes 54. Common reference numbers, particularly with regard to the snap eyelets 66 and snap stud 68 are identical to hereinbefore referenced elements having the same character reference. In the embodiment shown, the electrodes 54 may be cooperating electrodes, such as an anode and cathode, or be independent, such as a stimulation electrode, monitoring electrode or drug delivery electrode.

In the embodiment 22 fastener tabs 90 are utilized for securing the cover 86 directly to the member 12. An asymmetric pattern of the tabs 90 may be used to orient the cover 86, with the electrodes 54 attached thereto, within the opening 84. Alternatively, an indexed tab 92 and index 94 may be used for orientation.

Figure 9:
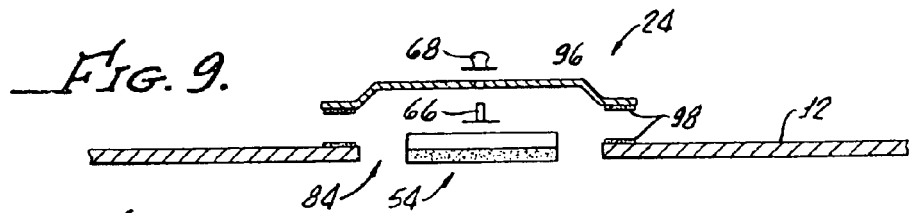
FIG. 9 is a cross-sectional exploded view of an alternative embodiment of an access window and cover in accordance with the present invention.
Figure 10:
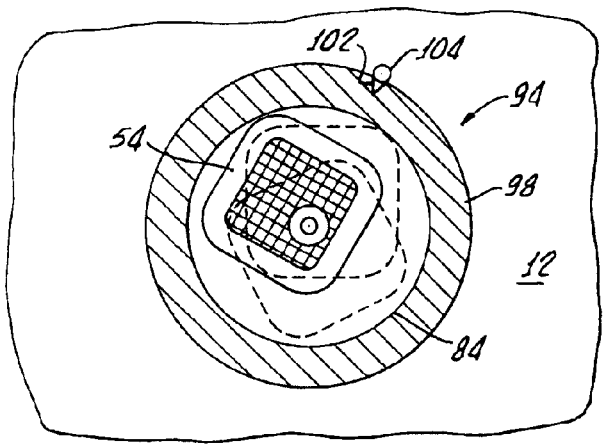
FIG. 10 is a plan view the embodiment shown in FIG. 9 along with an index marking for properly orienting the electrode within the access window.

With reference to FIGS. 9 and 10, there is shown alternative embodiment access window 24, that includes a removable cover 96 and an attachment system 98. As shown in FIG. 10, indicia 102, 104 disposed on the cover 98 and the garment member 12 may be utilized for alignment of the electrode 54 when the cover 96 is removed and replaced on to the garment member 12.

Figure 11:
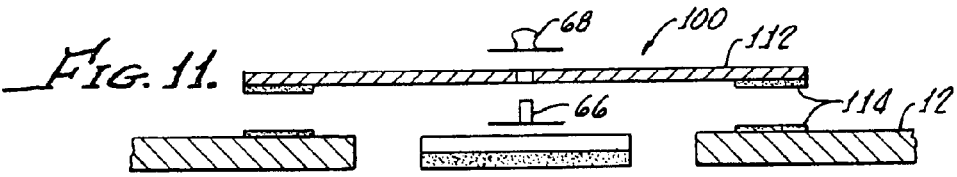
FIG. 11 is an alternative embodiment of a cover window access in accordance with the present invention.
Figure 12:
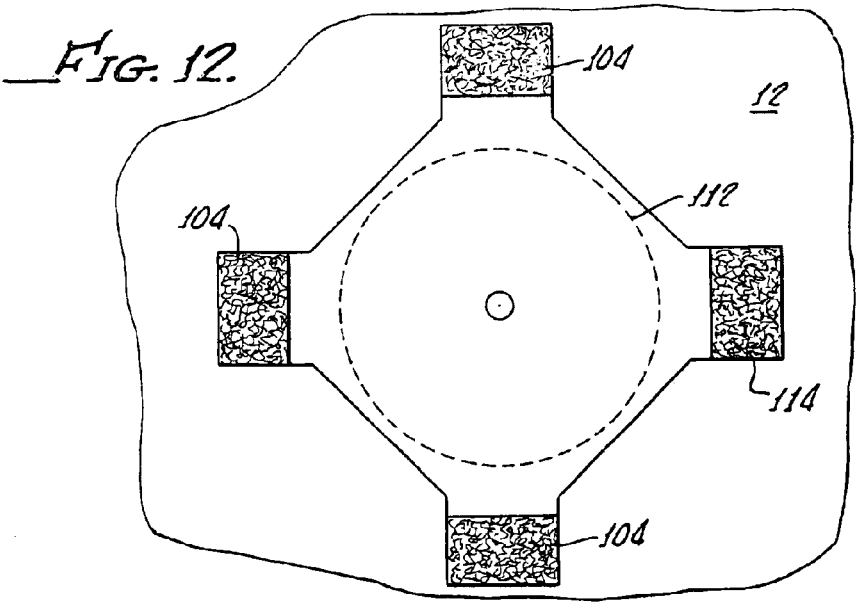
FIG. 12 is a plan view of the embodiment shown in FIG. 11.

With reference to FIGS. 11 and 12, there is shown an alternate embodiment of window access 100 (which generally includes a cover 102) which is secured to the garment member 12 by an attachment system 104. Common reference numerals refer to identical or substantially similar elements as hereinbefore described.

As shown in FIG. 12, the arrangement facilitates manufacture through the use of rectangular attachment pieces.

Figure 13:
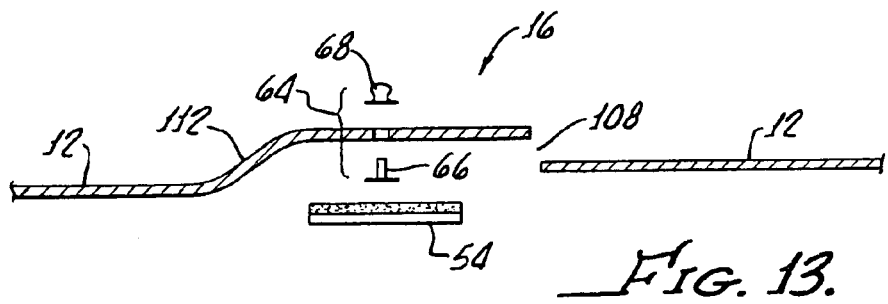
FIG. 13 is a cross-sectional exploded view of a slit access window in accordance with the present invention.
Figure 14:
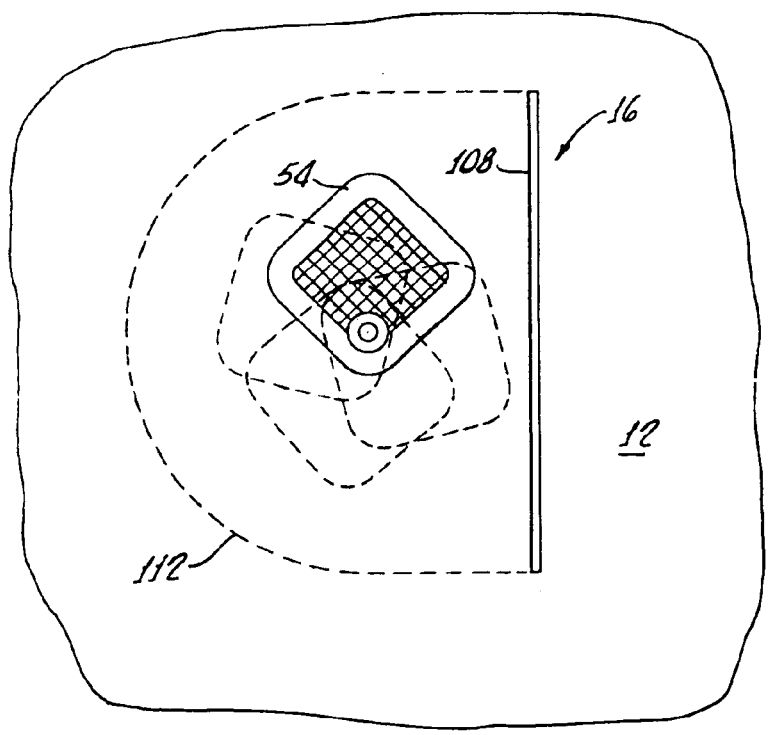
FIG. 14 is a plan view of the slit access window shown in FIG. 13.

With reference to FIGS. 13 and 14, the slit window access 16, which includes a slit 108 in the garment member, is disclosed. The elastic nature of the garment member 12 enables a stretching as indicated by the bend 112 in FIG. 13 enables the insertion of the electrode 54. The electrical connecter 64 comprising the eyelet 66 and snap stud 68 pass through the garment member 12 proximate the slit 108 for establishing electrical contact with the electrode 54. Again, reference numerals represent identical or substantial component as hereinabove described.

Although there has been hereinabove described a compress garment in accordance with the present invention, for the purpose of illustrating the manner in which the invention may be used to advantage, it will be appreciated that the invention is not limited thereto. Accordingly, and all modifications, variations or equivalent arrangements which may occur to those skilled in the art, should be considered to be within the scope of the invention as defined in the appended claims.

What is claimed is:

1. A compress garment for application to a body, said compress garment comprising:

a member sized and shaped for positioning onto a body and, in position, conforming to and supporting a body shape;

at least one access window disposed in said member and sized and shaped for enabling dermal application of a medical electrode with a gel and removal of the medical electrode, the access window being located on said member at a position enabling access to a preselected dermal area, said access window comprising an opening in said member, said opening being sized and shaped for enabling insertion and removal of said medical electrode and the garment further comprise a cover sized for covering said opening and said medical electrode, said opening being of sufficient size to enable placement of the electrode in various orientations under said cover, said electrode having smaller overall dimensions than an opening size; and an electrical contact, passing through said cover, for establishing electrical connection, exterior to said compress garment, with said medical electrode.

2. The compress garment according to claim 1 wherein the opening is sized for enabling application of multiple electrodes.

3. The compress garment according to claim 1 further comprising a carrier attached to said member for supporting an electronic module for connection to the medical electrode.

* * * * *